United States Patent [19]
Franberg et al.

[11] Patent Number: 5,417,716
[45] Date of Patent: May 23, 1995

[54] HEART STIMULATOR

[75] Inventors: Per Franberg, Stockholm; Lennart Moberg, Spanga; Anders Lindgren, Taeby, all of Sweden

[73] Assignee: Siemens Elema AB, Solna, Sweden

[21] Appl. No.: 152,125

[22] Filed: Nov. 16, 1993

[30] Foreign Application Priority Data

Nov. 25, 1992 [SE] Sweden ............... 92035427

[51] Int. Cl.⁶ ............................................. A61N 1/368
[52] U.S. Cl. ............................................................ 607/9
[58] Field of Search ........................................ 607/9, 16

[56] References Cited

U.S. PATENT DOCUMENTS

| | | | |
|---|---|---|---|
| 3,431,912 | 3/1969 | Keller, Jr. ................... | 607/9 |
| 4,030,510 | 6/1977 | Bowers ....................... | 607/9 |
| 4,284,082 | 8/1981 | Funke et al. ................ | 607/9 |
| 4,363,325 | 12/1982 | Roline et al. .............. | 607/9 |
| 4,572,193 | 2/1986 | Mann et al. ................. | 607/9 |
| 5,016,630 | 5/1991 | Moberg ........................ | 607/9 |

FOREIGN PATENT DOCUMENTS

WO92/16258  10/1992  WIPO .................... 607/9

Primary Examiner—William E. Kamm
Assistant Examiner—Marianne Parker
Attorney, Agent, or Firm—Hill, Steadman & Simpson

[57] ABSTRACT

In a heart stimulator which delivers stimulation pulses to a heart when the heart's spontaneous rate drops below a defined basic rate, in order to reduce the period during which the heart stimulator emits stimulation pulses, the defined basic rate is slow. When the spontaneous heart rate drops below the defined basic rate, stimulation pulses are initially emitted at a faster stimulation rate, in relation to the basic rate, the stimulation rate then dropping toward the defined basic rate.

12 Claims, 1 Drawing Sheet

HEART STIMULATOR

BACKGROUND OF THE INVENTION

1. Field of the Invention

The present invention relates to a heart stimulator of the type having a pulse generator for generating and delivering stimulation pulses to a heart, at least one detector for sensing events in the heart and a control device for controlling the pulse generator's emission of stimulation pulses according to events sensed by the detector, the pulse generator emitting stimulation pulses if a spontaneous heart rate, among events sensed by the detector, drops below a defined basic rate.

2. Description of the Prior Art

A heart stimulator of the type described above is generally referred to as "inhibiting," i.e., it inhibits emission of stimulation pulses as long as the heart naturally operates at an adequate beat rate. The heart stimulator can be for single chamber pacing or dual chamber pacing. The operating mode is designated with a three-letter alphabetic code in which the first letter designates the site of stimulation, A therefore designating an atrial site, V designating a ventricular site and D designating both atrial and ventricular sites, the second letter designates the site of sensing and the third letter designates the response to signals, I designating inhibition. Thus, AAI is a heart stimulation mode in which the atrium is stimulated and sensed and in which stimulation pulses are inhibited when spontaneous events are detected. VVI is the same mode although with a ventricular site, and DDI applies to both the atrium and the ventricle. DDI requires a dual chamber stimulator, whereas AAI and VVI can be programmed in both single chamber and dual chamber stimulators.

Stimulation pulses are emitted at a basic rate when the spontaneous heart rate drops below the basic rate. The basic rate is normally 60 to 80 beats/min. The heart stimulator can be programmed with hysteresis to prevent competitive stimulation when the spontaneous heart rate oscillates around the defined basic rate. The hysteresis rate is a rate slower than the basic rate. The spontaneous heart rate must then drop below this slower rate before stimulation pulses are emitted.

One type of pathological condition in the heart, the vasovagal syndrome, is manifested in a sudden drop in the spontaneous heart rate, causing the patient to faint, followed by restoration of the normal rate in a few seconds or minutes. The speed with which the spontaneous heart rate drops varies from one patient to another. Patients with this condition are generally provided with a heart stimulator which stimulates the heart when the spontaneous rate plummets to keep the patient from fainting. In known heart stimulators currently available, the spontaneous heart rate, once the heart stimulator has begun stimulation, must exceed the stimulation rate before the inhibiting function is reactivated so as to "silence" the stimulator. Thus, stimulation of the heart could still continue, even after the spontaneous heart rate has normalized.

Since people with this type of heart condition do not normally have any other heart defects, limiting stimulation to the briefest periods possible would be advantageous.

SUMMARY OF THE INVENTION

An object of the present invention is to provide a heart stimulator in which stimulation periods are limited to durations which are no longer than necessary.

This object is achieved in a heart stimulator constructed in accordance with the principles of the present invention wherein a heart stimulator of the above-described general type has a control device which induces the pulse generator, when the detected spontaneous heart rate drops below the defined basic rate, to emit stimulation pulses at a faster stimulation rate in relation to the defined basic rate. The stimulation rate subsequently slows down to the defined basic rate.

A slower basic rate can more appropriately be used in the heart stimulator of the invention than in prior art heart stimulators. Stimulation pulses are then emitted at a faster rate (which serves the function of the basic rate in the prior art), by the faster rate then slowing until it reaches the defined basic rate or until the spontaneous heart rate exceeds the stimulation rate. For patients with the above-described type of heart defect in which the heart rapidly recovers and then operates normally, the heart stimulator according to the present invention institutes the inhibiting function much earlier than in a prior art heart stimulator. The speed at which the increased stimulation rate drops to the defined basic rate can be fast or slow and is appropriately programmable so it can be adapted to different patients.

Preferably, the defined basic rate is slower than a spontaneous resting rate for the heart, preferably between 30 and 60 pulses/minute.

A basic rate slower than the patient's resting pulse ensures that no unnecessary stimulations are supplied.

Alternatively, the basic rate can be established by including an averager in the control device which calculates the average value for the spontaneous heart rate over a defined number of preceding heart cycles, the control device then setting the defined basic rate at the calculated average value less a defined value.

This approach directly adapts the basic rate to the spontaneous heart rate. The spontaneous heart rate is, e.g., slower at night than in daytime, and the basic rate would be adapted to this circumstance. The use of an averager value keeps the basic rate from changing too rapidly. Defined intervals for the basic rate can also be established to prevent the rate from, e.g., becoming too fast when the patient is very active for a long period of time.

In a further embodiment of the heart stimulator in accordance with the invention, the increased stimulation rate is programmable in the control device.

The faster stimulation rate can be established for each patient and programmed into the heart stimulator by a physician.

Alternatively, the faster stimulation rate can be established by including means in the control device for determining the spontaneous heart rate and setting the faster heart rate equal to the established spontaneous heart rate.

When the spontaneous heart rate drops suddenly, the heart is initially stimulated at the same rate, providing a more natural transition from spontaneous activity to stimulation.

In this circumstance, the control device sets the faster stimulation rate equal to the established spontaneous heart rate plus/minus a defined rate margin, the defined rate margin consisting of either a fixed value or a percentage of the detected spontaneous heart rate.

A third way of establishing the faster stimulation rate is to provide an activity sensor which senses the level of physical activity of the heart stimulator patient, and the control device sets the faster stimulation rate according to the sensed level of activity. The sensor-controlled stimulation rate then corresponds to the spontaneous rate in the physical activity.

In another embodiment of the heart stimulator in accordance with the invention the control device controls the pulse generator to cause it to emit a defined number of stimulation pulses at the defined basic rate, when the spontaneous heart rate drops below the defined basic rate, before the pulse generator emits stimulation pulses at the faster stimulation rate.

If the patient's heart recovers quickly, one or two stimulation pulses may suffice until an adequate spontaneous heart rate reappears. Inhibition of the heart stimulator thus occurs more rapidly than if the faster stimulation rate were emitted immediately.

As in prior art heart stimulators, the control device can be programmed with a defined hysteresis rate which is slower than the defined basic rate, in which case the spontaneous heart rate must drop below the hysteresis rate in order for the pulse generator to emit any stimulation pulses.

For example, the hysteresis rate, in combination with a defined basic rate corresponding to a spontaneous resting heart rate, ensures that the spontaneous heart rate, e.g., at night, can be allowed to drop below the basic rate without emission of any stimulation pulses.

DESCRIPTION OF THE PREFERRED EMBODIMENTS

Figure 3:
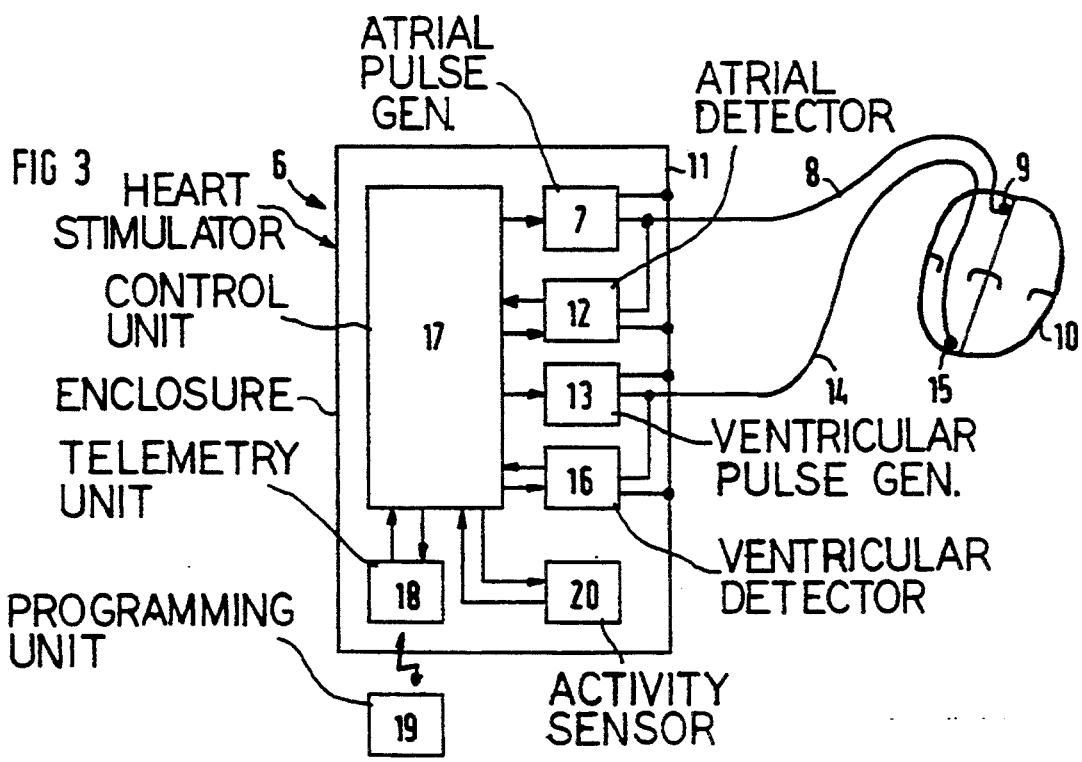
FIG. 3 is a schematic block diagram of one embodiment of the heart stimulator according to the invention.

The heart stimulator 6 in FIG. 3 has an atrial pulse generator 7 which generates atrial stimulation pulses and delivers same to the atrium in a heart 10 via a first electrode conductor 8 and a first tip electrode 9. The atrial stimulation pulses are then conducted through body tissue to the enclosure 11 of the heart stimulator 6, which serves as an indifferent electrode, and back to the atrial pulse generator 7. An atrial detector 12 is connected to the first electrode conductor 8 and the enclosure 11 for sensing events in the atrium.

In the corresponding manner, a ventricular pulse generator 13 generates ventricular stimulation pulses and delivers same to the ventricle in a heart 10 via a second electrode conductor 14 and a second tip electrode 15. The ventricular stimulation pulses are conducted back to the ventricular pulse generator 13 via body tissue and the enclosure 11 of the heart stimulator 6. A ventricular detector 16 is connected to the second electrode conductor 14 and the enclosure 11 for sensing events in the ventricle.

The pulse generators 7 and 13 and detectors 12 and 16 are controlled by a control device 17 which receives information on the events sensed by the detectors 12 and 16 in the heart 10.

The control device 17 can be programmed by a physician with different functions by means of a telemetry unit 18 in the heart stimulator 6 and an extracorporeal programming unit 19. The physician can, e.g., program the basic rate and operating mode, e.g., AAI, VVI or DDI.

A motion sensor 20 senses the level of physical activity of the heart stimulator patient, and this signal is sent to the control device 17 which can, dependent thereon, determine a faster stimulation rate at which the heart stimulator 6 is to stimulate the heart 10 when spontaneous activity ceases.

Figure 1:
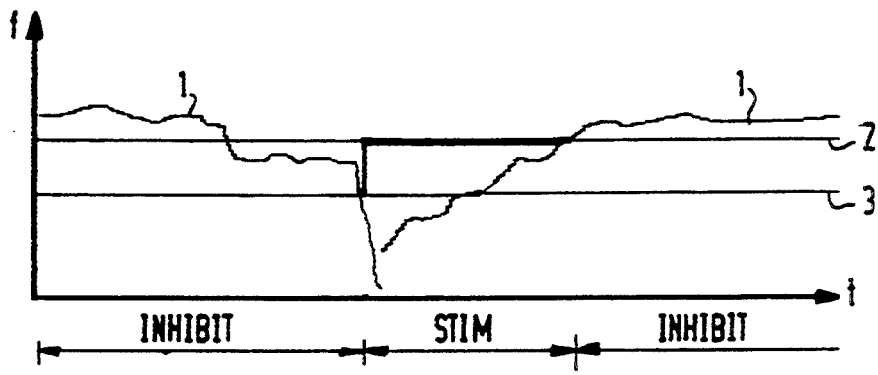
FIG. 1 is a diagram illustrating the functioning of a heart stimulator according to the prior art.

A spontaneous heart rate signal 1 in a frequency-time (f-t) diagram is shown in FIG. 1. The levels for a basic rate 2, e.g. 80 pulses/minute, and a hysteresis rate 3, e.g. 50 pulses/minute, programmed in a prior art heart stimulator are also shown in the diagram. The heart stimulator inhibits emission of stimulation pulses as long as the spontaneous heart rate 1 is faster than the hysteresis rate 3.

Due to one type of pathological condition in a heart, the spontaneous heart rate 1 can drop suddenly and return to a normal rate and normal function a few seconds to a few minutes later. When this happens to the spontaneous heart rate 1 in FIG. 1, the heart stimulator according to the prior art stimulates the heart at the basic rate 2, as marked in the diagram with a bolder basic frequency line. The spontaneous heart rate 1, marked during the period of stimulation, illustrates restoration of normal cardiac function. Since stimulation occurs at a faster rate, and each stimulation resets, so to speak, biologically spontaneous functioning, the spontaneous heart rate 1 during stimulation cannot usually be visualized. In, e.g., the heart stimulator's VVI mode, the spontaneous heart rate signal 1 would show the atrium's recovery. Spontaneous activity must exceed the basic rate 2 for termination of stimulation pulses, the heart stimulator again being inhibited until the next time the spontaneous heart rate 1 drops below the hysteresis rate 3. Periods of inhibition (INHIBIT) and stimulation (STIM) are shown on the time axis t.

Figure 2:
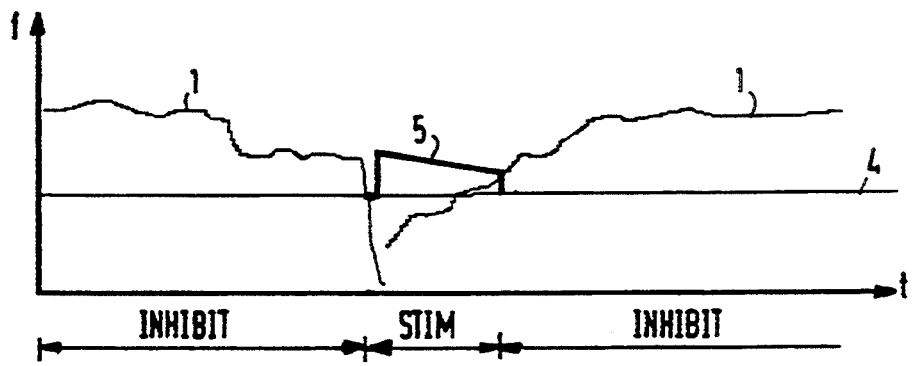
FIG. 2 is a diagram illustrating the functioning of the heart stimulator according to the invention.

FIG. 2 shows the same spontaneous heart rate signal 1 in an f-t diagram to illustrate how the heart stimulator 6 according to the present invention operates under the same circumstances. Another basic rate, e.g. 50 beats/min, is drawn in the diagram. In contrast to the basic rate 2 in FIG. 1, the basic rate 4 is, according to the invention, much slower. In principle, no hysteresis rate is necessary, but one could be used to avoid unnecessary stimulation, e.g. during sleep when the spontaneous heart rate 1 can drop below the basic rate 4.

When the spontaneous heart rate 1 drops below the basic rate 4, the heart stimulator 6 initially emits a few stimulation pulses at the basic rate. This is to give the heart time to terminate the stimulation function if it recovers rapidly. The heart stimulator 6 thereafter continues stimulation at a faster rate 5 which subsequently slows. The faster rate 5 can be initially programmed at e.g., 80 beats/minute or, if the heart stimulator 6 senses the spontaneous rate 1, can be set on the basis of the latest spontaneous heart rate 1 which is sensed. The faster stimulation rate can also be determined by the control device 17 according to the level of sensed activity from the sensor 20.

In this instance, the faster stimulation rate 5 is based on the latest spontaneous heart rate 1 sensed plus a defined rate margin. The faster stimulation rate 5 slows until it reaches the basic rate 4 or until the spontaneous heart rate 1 is again fast enough to activate the inhibiting function of the heart stimulator 6. As the period designation under the time axis t show, the stimulation period (STIM) is shorter than in a prior art stimulator.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulator comprising:
   pulse generator means for generating and emitting stimulation pulses to a heart at a rate;
   detector means for sensing events in said heart, including spontaneous heartbeats; and
   control means, connected to said pulse generator means and to said detector means, for controlling the emission of stimulation pulses by said pulse generator means for causing the emission of a stimulation pulse if a spontaneous heartbeat rate as sensed by said detector means drops below a defined basic rate and for causing said pulse generator means, when said spontaneous heartbeat rate falls below said defined basic rate, to emit said stimulation pulses at a rate faster than said defined basic rate and for subsequently slowing the rate of emission of said stimulation pulses down to said defined basic rate.

2. A heart stimulator as claimed in claim 1 wherein said heart has a spontaneous resting rate, and wherein said defined basic rate is slower than said spontaneous resting rate.

3. A heart stimulator as claimed in claim 1 wherein said defined basic rate is between 30 and 60 pulses per minute.

4. A heart stimulator as claimed in claim 1 wherein said control means includes averaging means for calculating an average value of said spontaneous heartbeat rate over a selected number of heart cycles, and for then setting said defined basic rate at said calculated average value less a defined value.

5. A heart stimulator as claimed in claim 1 further comprising means for programming said faster stimulation rate into said control means.

6. A heart stimulator as claimed in claim 1 wherein said control means comprises means for identifying said spontaneous heartbeat rate and for setting said faster stimulation rate equal to said spontaneous heartbeat rate.

7. A heart stimulator as claimed in claim 1 wherein said control means comprises means for identifying said spontaneous heartbeat rate and for setting said faster stimulation rate equal to said spontaneous heartbeat rate plus or minus a defined rate margin.

8. A heart stimulator as claimed in claim 1 wherein said control means comprises means for identifying said spontaneous heartbeat rate and for setting said faster stimulation rate equal to said spontaneous heartbeat rate plus or minus a defined rate margin consisting of a fixed value.

9. A heart stimulator as claimed in claim 1 wherein said control means comprises means for identifying said spontaneous heartbeat rate and for setting said faster stimulation rate equal to said spontaneous heartbeat rate plus or minus a defined rate margin which is a percentage of said spontaneous heartbeat rate.

10. A heart stimulator as claimed in claim 1 further comprising activity sensor means for sensing a level of physical activity in a patient whose heart is to be stimulated, and wherein said control means comprises means for setting said faster stimulation rate dependent on the level of activity sensed by said physical activity sensor means.

11. A heart stimulator as claimed in claim 1 wherein said control means comprises means for causing said pulse generator means to emit a selected number of stimulation pulses at said defined basic rate, when said spontaneous heartbeat rate falls below said defined basic rate, before causing said pulse generator means to emit stimulation pulses at said faster stimulation rate.

12. A heart stimulator as claimed in claim 1 comprising means for programming a defined hysteresis rate into said control means which is slower than said defined basic rate, and wherein said control means includes means for requiring said spontaneous heartbeat rate to fall below said hysteresis rate before causing said pulse generator means to emit any stimulation pulses.

* * * * *